(12) United States Patent
Bach et al.

(10) Patent No.: US 7,309,508 B2
(45) Date of Patent: Dec. 18, 2007

(54) NON-LAURIC, NON-TRANS, NON-TEMPER FAT COMPOSITIONS

(75) Inventors: Mogens Bach, Aarhus (DK); Bjarne Juul, Tranbjerg (DK)

(73) Assignee: Aarhuskarlshamn Denmark A/S (DK)

( * ) Notice: Subject to any disclaimer, the term of this patent is extended or adjusted under 35 U.S.C. 154(b) by 590 days.

(21) Appl. No.: 10/832,344

(22) Filed: Apr. 27, 2004

(65) Prior Publication Data

US 2005/0142275 A1 Jun. 30, 2005

Related U.S. Application Data

(63) Continuation of application No. PCT/DK02/00728, filed on Nov. 1, 2002.

(60) Provisional application No. 60/331,713, filed on Nov. 21, 2001.

(51) Int. Cl.
*A23D 9/00* (2006.01)
(52) U.S. Cl. .................................. 426/607; 426/601
(58) Field of Classification Search ............. None
See application file for complete search history.

(56) References Cited

U.S. PATENT DOCUMENTS

| | | | | |
|---|---|---|---|---|
| 4,214,012 | A | 7/1980 | Ainger et al. | 426/607 |
| 4,726,959 | A | 2/1988 | Momura et al. | 426/607 |
| 4,839,192 | A | 6/1989 | Sagi et al. | 426/607 |
| 5,288,513 | A | 2/1994 | Cain et al. | 426/660 |
| 5,405,639 | A | 4/1995 | Pierce et al. | 426/607 |
| 5,424,091 | A | 6/1995 | Cain et al. | 426/610 |
| 5,508,048 | A | 4/1996 | Padley | 426/33 |
| 5,731,027 | A | 3/1998 | Cain et al. | 426/607 |
| 5,972,412 | A | 10/1999 | Sassen et al. | 426/603 |
| 6,033,695 | A | 3/2000 | Cain et al. | 426/89 |
| 6,258,398 | B1 | 7/2001 | Okada et al. | 426/607 |
| 6,277,433 | B1 | 8/2001 | Lantz et al. | 426/606 |

FOREIGN PATENT DOCUMENTS

| | | |
|---|---|---|
| EP | 0 536 824 | 4/1993 |
| GB | 2 297 760 | 8/1996 |

OTHER PUBLICATIONS

Hashimoto, S. et al, JAOCS, vol. 78(5), 2001, pp. 455-460.
Hachiya, I. et al, JAOCS, vol. 66(12), 1989, pp. 1763-1770.

*Primary Examiner*—Carolyn Paden
(74) *Attorney, Agent, or Firm*—Steptoe & Johnson LLP

(57) ABSTRACT

A non-lauric, non-trans, non-temper (Non-LTT) fat composition comprising a fraction obtained from a randomised triglyceride mixture in which min. 90% by weight of the constituent fatty acids are: palmitic (C16:0), stearic (C18:0), arachidic (C20:0) behenic (C22:0), oleic (C18:1) and linoleic (C18:2) acid and the total content of arachidic and behenic acid is 3-40% by weight and the total content of palmitic and stearic acids is 25-60% by weight, said fraction having the following physical and chemical properties: (1) slip melting point measured according to AOCS Cc 3-25: below 36° C. and solid fat content (SFC) measured according to IUPAC 2.150 mod. (stabilised at 20° C. for 24 h): above 25% by weight at 20° C.; (2) total content of saturated fatty acids measured according to IUPAC 2.301 and 2.304: 40-75% by weight, preferably 45-70% by weight; (3) total content of arachidic and behenic acids: 3-40% by weight, preferably 5-35% by weight, and total content of palmitic and stearic acids: 25-60% by weight, preferably 25-50% by weight, both measured according to IUPAC 2.301 and 2.304; (4) total content of triglycerides having triglyceride composition (TGC) of C56-C60 measured by number of total carbon atoms of constituent fatty acids according to IUPAC 2.323: min. 9% by weight, preferably min. 15% by weight; (5) total content of $S_2U$-type triglycerides: min. 25% by weight, preferably min. 35% by weight, where S=saturated fatty acids and U=unsaturated fatty acids.

28 Claims, 3 Drawing Sheets

Fig. 2
Fig. 2-1
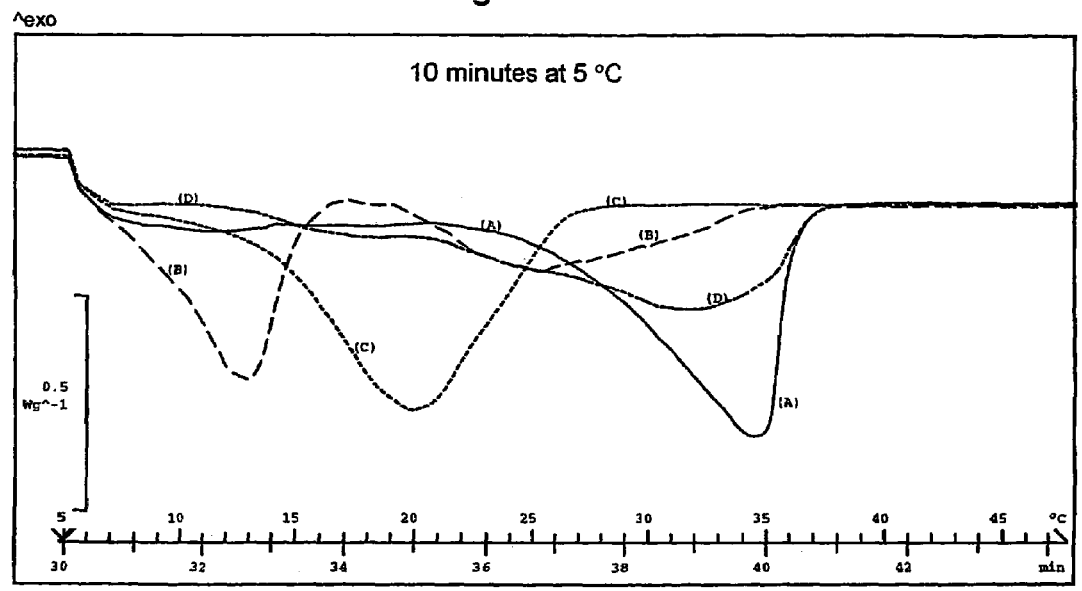
Fig. 2-2
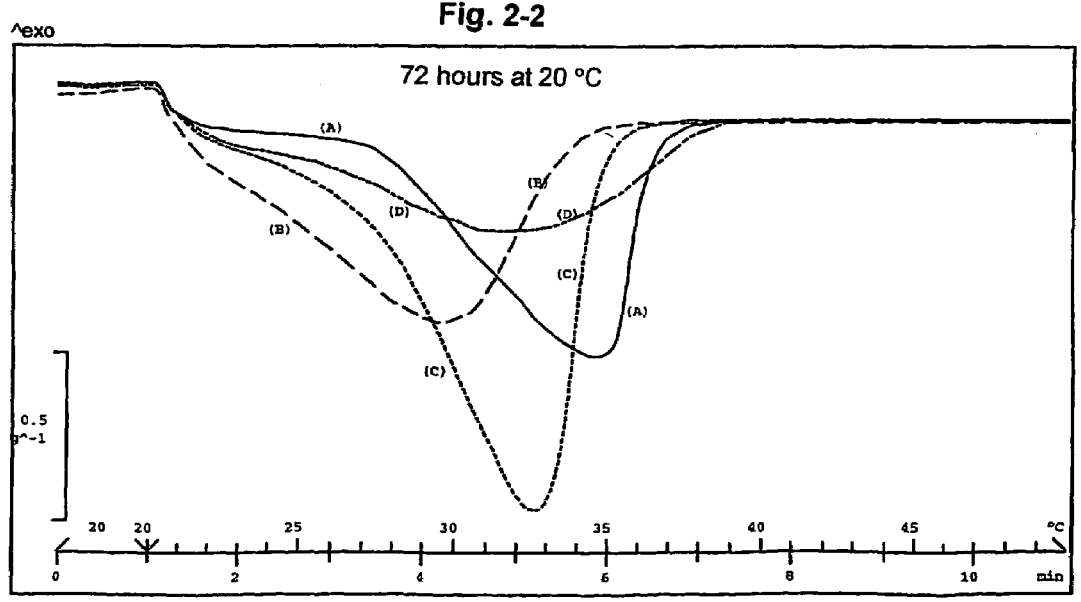

NON-LAURIC, NON-TRANS, NON-TEMPER FAT COMPOSITIONS

This application is a continuation of International Application PCT/DK02/00728, filed Nov. 1, 2002, which application claims the benefit of U.S. Provisional Application Ser. No. 60/331,713, filed Nov. 21, 2001, and Danish Application PA 2001 01634, filed Nov. 2, 2001.

FIELD OF THE INVENTION

The present invention relates to non-lauric, non-trans, non-temper (Non-LTT) fat compositions having the advantage of fast crystallisation in a stable form. The predominant fatty acid moieties of the triacylglycerols (TAG) in the fat compositions are: palmitic, stearic, arachidic, behenic, oleic and linoleic acid. The fat compositions are useful in food and non-food applications.

BACKGROUND OF THE INVENTION

The high-melting fractions of lauric oils, e.g. palm kernel oil, are known as cocoa butter substitutes (CBS). They are used as ingredients in confectioneries, suppositories, lip balms, etc.

Lauric CBSs solidify in a stable crystal form, which does not require a complicated "tempering". Tempering is the controlled formation of a sufficient number of stable seed crystals that ultimately produce the desired crystal form during solidification. Some of the main drawbacks are low cocoa butter tolerance, and when used as filling fat it will migrate into the surrounding chocolate shell, eventually leading to bloom. Furthermore, when exposed to moisture and if fat splitting enzymes are present, there is a risk of hydrolysis giving the product an undesirable, soapy flavour.

Non-lauric, non-temper alternatives to CBSs are trans-hydrogenated and, usually, fractionated triglyceride mixtures based on soybean oil, rapeseed oil, sunflower oil, palm oil or other similar oils and fats. They are known as non-lauric CBSs or cocoa butter replacers (CBR) with a fair cocoa butter tolerance. They are non-temper fats, but they have a slower solidification rate than lauric CBS. Furthermore, they suffer from the drawback of containing trans fatty acids in the glycerides that are suspected of increasing the blood cholesterol level and the risk of coronary heart disease if contained in the diet. As a result of this, consumers are increasingly looking for foods without these fatty acids.

Non-trans, non-lauric alternatives are cocoa butter (CB) and cocoa butter equivalents (CBE). The production of CBEs is based on fractions of fats containing the same triglycerides as CB, e.g. palm oil, shea butter, illipe, etc. The main part of the triglycerides is of the symmetric SUS type (S=saturated fatty acids, U=unsaturated fatty acids) or more specifically, StOSt, POSt and POP (P=palmitic acid, St=stearic acid, O=oleic acid).

CB and CBE exist in a number of polymorphic forms, and the nature of the crystalline form depends on the method of cooling of the liquid fat. If the fat is allowed to crystallise in an unstable form, it recrystallises after a time delay. In the production of chocolate this transformation will cause a change from a nice glossy chocolate to a dull or mouldy looking chocolate. This phenomenon, "fat-bloom", is avoided by tempering of the chocolate. In the tempering process the liquid chocolate is cooled down to produce both stable and unstable crystals followed by heating to a temperature above the melting point of the unstable crystals, leaving only stable seed crystals.

Tempering is a complicated and expensive process, and consequently there is a need for fat compositions that do not require tempering and do not contain lauric and trans fatty acids.

DESCRIPTION OF RELATED ART

Fats that do not contain trans fatty acids can be obtained by dry and/or solvent fractionation of oils with a natural content of higher melting triglycerides. Non-lauric fats can be produced by fractionation of suitable oils, e.g. palm oil. Palm-midfractions (PMF) are known in the industry. PMF is rich in the SUS type of triglycerides of which POP is predominant. The PMFs are suffering from the drawback that they need pre-crystallisation or seeding to crystallise fast in a stable form. Without pre-crystallisation or seeding during cooling the PMF will re-crystallise leading to bloom when used in chocolate or post-hardening when used as a filling fat or as hardstock in margarine.

Preparation of hard PMF and its use as non-lauric CBS in chocolate is described in literature (Satsuki Hashimoto et al. 2001. JAOCS vol. 78 (5), 455-460). It was experimentally demonstrated that PMFs with a high content of POP and StOP produce chocolate just as good as conventional CB based chocolate, except for a reduction in bloom resistance. Addition of 1% by weight polyglycerol fatty acid ester (i.e. hexaglycerol octastearate) as anti-bloom agent improved the stability to an extent that was expected to be sufficient for commercial use.

EP 1 038 444 A1 teaches how to produce hard butter compositions by the fractionation of soft PMF. To the hard butter is added 1-5% by weight, more preferably 2.5-5% by weight, polyglycerol fatty acid esters with a polymerisation degree of glycerol of 4-8, whose fatty acid residues are exemplified by: palmitic, stearic, oleic or behenic acid. The emulsifier added acts as a bloom retardant. The fat compositions are used in chocolate.

Seeding effects and fat bloom properties of dark chocolate are described in literature (Iwao Hachiya et al. 1989. JAOCS vol. 66 (12), 1763-1770). In the experiments CB powder (form VI), StOSt powder ($\beta_1$ form), BOB (B=behenic acid) powder (pseudo-$\beta'$ and $\beta_2$ form) and StStSt powder ($\beta$ form) were used as seed crystals. The fat bloom stability was tested, and in a 38° C./20° C. cycle test, BOB ($\beta_2$ form) proved to be the best seed material to prevent fat bloom at a concentration of 5% by weight.

U.S. Pat. No. 4,726,959 teaches a fat blooming inhibitor comprising a mixture of triglycerides, said mixture containing from 40 to 100% by weight of a mixed-acid triglyceride component that contains, in the same molecule as different fatty acid moieties, both saturated fatty acids having from 20 to 24 carbon atoms and unsaturated fatty acids having from 16 to 22 carbon atoms, the amount of said saturated fatty acids in said mixture being from 15 to 70% by weight and the amount of said unsaturated fatty acids in said mixture being from 20 to 60% by weight, both percentages being based on the total weight of the fatty acid moieties present in said mixture. The fat mixture defined by the claims is stated to be a fat blooming inhibitor which may be added to a hard butter product such as chocolate in an amount of 0.5 to 30% by weight, preferably 2 to 20% by weight, and it appears from the Synthesis Examples 1-5 and Table 1 that the melting point of the inhibitor is 36.0° C. or higher.

U.S. Pat. No. 4,839,192 teaches a hard buffer composition for use in confectionery such as chocolate where it improves high-temperature resistance and anti-bloom properties. The main ingredient of the composition is SUS-type of triglycerides. The SUS amount is 50% by weight or more, more preferably 65% by weight or more. The constituent saturated fatty acids thereof comprise 4-30% by weight of one or more fatty acids selected from the group consisting of behenic, lignoceric, cerotic, and arachidic acid. The fat having the desired triglyceride composition can be produced by selective transesterification of monovalent alcohol esters of the above mentioned fatty acids into α and α' positions of a fat or oil rich in unsaturated fatty acid residues in the β position thereof. In the reference example 3 it is shown that non-selective random transesterification, even after solvent fractionation was carried out, resulted in a product that had poor miscibility with CB (i.e. difficulty in uniform crystallisation) and inferior melting properties in the mouth. The hard butter of the invention can optionally be mixed with other SUS rich fats such as PMF to give the hard butter composition of the invention.

EP 0 536 824 A1 teaches a fat that does not need to be tempered and does not contain trans fatty acids or lauric fats. The fat composition consists predominantly of triglycerides with more than 50% by weight SUS-type triglycerides that are capable of crystallising in the β crystal form. The composition also contains an externally added, minimal working amount of a fat component, capable of stabilizing $β^1$ crystals, which comprises at least a vegetable triglyceride of the SSO-type and/or of the $S_3$-type, also containing an SOO-type triglyceride in such an amount that the weight ratio SSO:SOO is at least 3.0, preferably at least 5.0, while the St:P weight ratio of the total fat composition is less than 1.0. Hereby S=a saturated fatty acid $C_{10}$-$C_{24}$, U=an unsaturated fatty acid $C_{18}$-$C_{22}$, O=oleic acid, P=palmitic acid, and St=stearic acid, and any combination of fatty acids can be present in SSO and $S_3$. Although the triglycerides capable of crystallising in the β form will in general comprise some SSO and/or SSS, the amount is insufficient to stabilise the $β^1$ form. Therefore, it is necessary to add externally an effective amount of SSO or SSS, or a mixture thereof. The amount of SSO in the total fat composition should be 8-40% by weight, preferably 10-20% by weight. The SSO component is preferably derived from palmitic and/or stearic as saturated fatty acids. The best results are obtained in combination with an SSS fat. The amount of SSS is 2-20% by weight, preferably 3-15% by weight. An example of such a fat, which can be obtained from the hardening of PMF, is PStP. A preferred amount of PStP is 2-10% by weight on the total fat in the composition. From the example, it can be deduced that triglycerides with saturated fatty acids of $C_{20}$ or higher are limited to less than 2% by weight of the total fat composition.

EP 0 555 917 A1 teaches a cool-melting, non-temper, non-trans filling fat comprising a fat blend having the following composition:

35-80 wt. %, preferably 51-80 wt. %, and most preferably 55-70 wt. %, of SUS;
less than 5 wt. %, preferably less than 3 wt. %, of $S_3$';
7-60 wt. %, preferably 10-50 wt. %, of ($U_2S+U_3$);
less than 40 wt. % of SSU;
the weight ratio SUS/SSU being <6, wherein
S=saturated fatty acid having 16-18 C atoms;
S'=saturated fatty acid having 10-24 C atoms;
U=unsaturated fatty acid having 16-22 C atoms, in particular $C_{18:1}$.

The preferred fat compositions are derived from palm fat so that the SUS component of the fat is mainly POP.

GB 2 297 760 A teaches behenic acid containing fats especially suited for confectionery coatings. As the main fatty acid constituents the fats comprise behenic acid, oleic acid and, optionally, stearic acid. The content of behenic acid is min. 25% by weight, and the total content of saturated fatty acids is less than 45% by weight. The fats contain at least 40% by weight of BOO triglycerides and preferably more than 20% by weight BOSt triglycerides. It is, however, preferred to apply fats with a BOO/BOSt ratio of more than 1.8. The fats can be made by interesterification of a natural fat with a free fatty acid or a derivative thereof. This is illustrated in examples 1 and 2 where high oleic sunflower oil or an oleine rich in StOO is reacted with behenic acid in the presence of a 1,3-specific lipase.

WO 95/14392 teaches blends of a sugar and a triglyceride component suitable for the preparation of filling fat compositions and ice-cream coatings with a low content of saturated fatty acids. The triglyceride component has a content of max. 45% by weight saturated fatty acids and comprises at least 40% by weight of $SU_2$ triglycerides and 3-50% by weight of $S_2U$ triglycerides. S being saturated fatty acids with 18-24 carbon atoms, and U being unsaturated fatty acids with 18 or more carbon atoms. Suitable triglyceride compositions are compositions rich in BOO, StOO, OStO, OBO or mixtures thereof. As the $S_2U$ component the composition will also contain BOB, BBO, StOSt or StStO. Such triglycerides can be made by interesterification of natural fats by using a fatty acid as a source for the fatty acid moiety, that has to be introduced into the natural fat. The triglyceride component contains at least 10% by weight of behenic acid, preferably at least 25% by weight. Filling fat compositions contain 35-75% by weight, preferably 40-65% by weight of the triglyceride component.

Ice-cream coating compositions contain 40-75% by weight of the triglyceride component.

OBJECTS OF THE INVENTION

One object of the invention is to provide non-lauric, non-trans fat compositions that have a fast crystallisation and solidify in a stable crystal form without any tempering or addition of seed crystals or anti-bloom agents.

Another object is to provide a range of non-lauric, non-trans, non-temper fat compositions with different melting behaviour to diversify the range of applications.

A further object of the invention is to provide non-lauric, non-trans, non-temper fat compositions having a high degree of compatibility with other fats that normally need tempering, e.g. CB and PMF, and the ability to entrap considerable amounts of foreign fats, e.g. milk fat, liquid oils, etc. without loosing the non-temper feature or the fast crystallisation behaviour.

SUMMARY OF THE INVENTION

We have found that the objectives are fulfilled by a non-lauric, non-trans, non-temper (Non-LTT) fat composition comprising a fraction obtained from a randomised triglyceride mixture in which min. 90% by weight of the constituent fatty acids are: palmitic (C16:0), stearic (C18:0), arachidic (C20:0), behenic (C22:0), oleic (C18:1) and linoleic (C18:2) acid and the total content of arachidic and behenic acid is 3-40% by weight and the total content of palmitic and stearic acids is 25-60% by weight, said fraction having the following physical and chemical properties:

(1) slip melting point measured according to AOCS Cc 3-25: below 36° C. and solid fat content (SFC) measured according to IUPAC 2.150 mod. (stabilised at 20° C. for 24 h): above 25% by weight at 20° C.;

(2) total content of saturated fatty acids measured according to IUPAC 2.301 and 2.304: 40-75% by weight, preferably 45-70% by weight;

(3) total content of arachidic and behenic acids: 340% by weight, preferably 5-35% by weight, and total content of palmitic and stearic acids: 25-60% by weight, preferably 25-50% by weight, both measured according to IUPAC 2.301 and 2.304;

(4) total content of triglycerides having triglyceride composition (TGC) of C56-C60 measured by number of total carbon atoms of constituent fatty acids according to IUPAC 2.323: min. 9% by weight, preferably min. 15% by weight;

(5) total content of $S_2U$-type triglycerides: min. 25% by weight, preferably min. 35% by weight, where S=saturated fatty acids and U=unsaturated fatty acids.

It is preferred that the molar content of behenic acid is higher than that of arachidic acid. Preferably, however, the total content of triglycerides having a TGC of C62 is max. 15% by weight.

Randomisation refers to a random distribution of the fatty acids on the glycerol molecules. Triglyceride mixtures resulting from the rearrangement of the six basic fatty acids will contain up to 126 different TAGs, without accounting for enatiomers.

Normally, a non-lauric fat should contain less than 4% by weight of lauric acid, and preferably the content of lauric acid is in the fat compositions according to the invention max. 1% by weight, more preferably max. 0.5% by weight.

A non-trans fat should contain less than 3% by weight of trans fatty acids, and preferably the total content of trans fatty acids in the fat compositions according to the invention is max. 1% by weight.

Further, in the fat compositions according to the invention the content of diglycerides generally is max. 10% by weight, preferably max. 5% by weight.

By Differential Scanning Calorimetry (DSC) performed in a Mettler Toledo Star System using the following T-regime: isotherm at 50° C. for 1 minute, cooling at a rate of 3° C./min, it was verified that the above mentioned fat compositions have an onset of crystallisation at relatively high temperatures in the range of 36-22° C. and that they crystallise in a stable form.

In dynamic, temperature controlled rheological measurements they displayed a rapid onset of crystallisation and a crystallisation rate comparable to that of trans-hydrogenated fats.

The Non-LTT fat compositions according to the invention can be prepared by randomising a triglyceride mixture in which min. 90% by weight of the constituent fatty acids are: palmitic (C16:0), stearic (C18:0), arachidic (C20:0), behenic (C22:0), oleic (C18:1) and linoleic (C18:2) acid and the total content of arachidic and behenic acid is 3-40% by weight and the total content of palmitic and stearic acids is 25-60% by weight and subsequently fractionating the randomised mixture to isolate a fraction having a slip melting point below 36° C. measured according to AOCS Cc 3-25 and having an onset of crystallisation in the temperature range of 36-22° C. by differential scanning calorimetry (DSC) performed in a Mettler Toledo Star System using the following T-regime: isotherm at 50° C. for 1 minute, cooling at a rate of 3° C./min.

Usually, the randomisation is done by a transesterification procedure using a catalyst such as an acid, alkaline or metal catalyst, preferably an alkali metal alkoxide, or an enzyme such as a lipase.

We have found that the non-temper characteristic is present in selected fractions of the randomised multi-component mixture of triglycerides. This makes it possible to ramify fat compositions to a variety of application areas.

The selected fractions of the invention can be obtained by removing the high melting TAGs or in another aspect the high melting and the low melting TAGs resulting in a mid-fraction.

The fat compositions of the invention have a high compatibility with other oils and fats. The non-temper properties are maintained in mixtures with fats high in SUS, e.g. CB and PMF, and in mixtures with oils high in UUU and SUU, e.g. hazelnut oil, peanut oil, etc. Consequently, the fat compositions are useful as ingredients in a broad range of food and non-food products.

Furthermore, the fat compositions of the invention exhibit anti-bloom effects when added in low concentrations to chocolate and chocolate-like products.

Part of the invention is the use of the fat compositions of the invention in food products, especially as an ingredient in confectionery, bakery and dairy fillings, confectionery coatings, etc.

Part of the invention is further the use of the fat compositions of the invention as a water barrier between materials with high and low humidity in confectionery and bakery products as well as a paper coating agent.

The use of the fat compositions of the invention in non-food products, e.g. as emollients, excipients and consistency giving ingredients in cosmetics and pharmaceuticals, is also part of the invention.

Further, the invention comprises a fat composition for confectionery applications comprising vegetable oil or fat and a Non-LTT fat according to any one of claims 1-7 in a ratio of 98-5% by weight vegetable oil or fat to 2-95% by weight Non-LTT fat, preferably 95-10% by weight vegetable oil or fat to 5-90% by weight Non-LTT fat, and more preferably 80-20% by weight-vegetable oil or fat to 20-80% by weight Non-LTT fat.

DESCRIPTION OF THE DRAWINGS

The drawings illustrate the characteristics of a fat of the invention in comparison with commercial available temper and non-temper fats.

The trade name and description of the products are summarised in the following:

Fat A: A non-lauric, non-trans, non-temper fat composition of the invention.

Fat B: "Centremelt H" (Loders Croklaan B.V.) is a non-lauric, non-trans and non-temper filling fat according to EP 0555917 B1.

Fat C: Cocoa Butter, West Africa.

Fat D: "Confao 30." (Aarhus Oliefabrik A/S) is a non-temper filling fat based on trans-hydrogenated oils of non-lauric origin.

Figure 1:
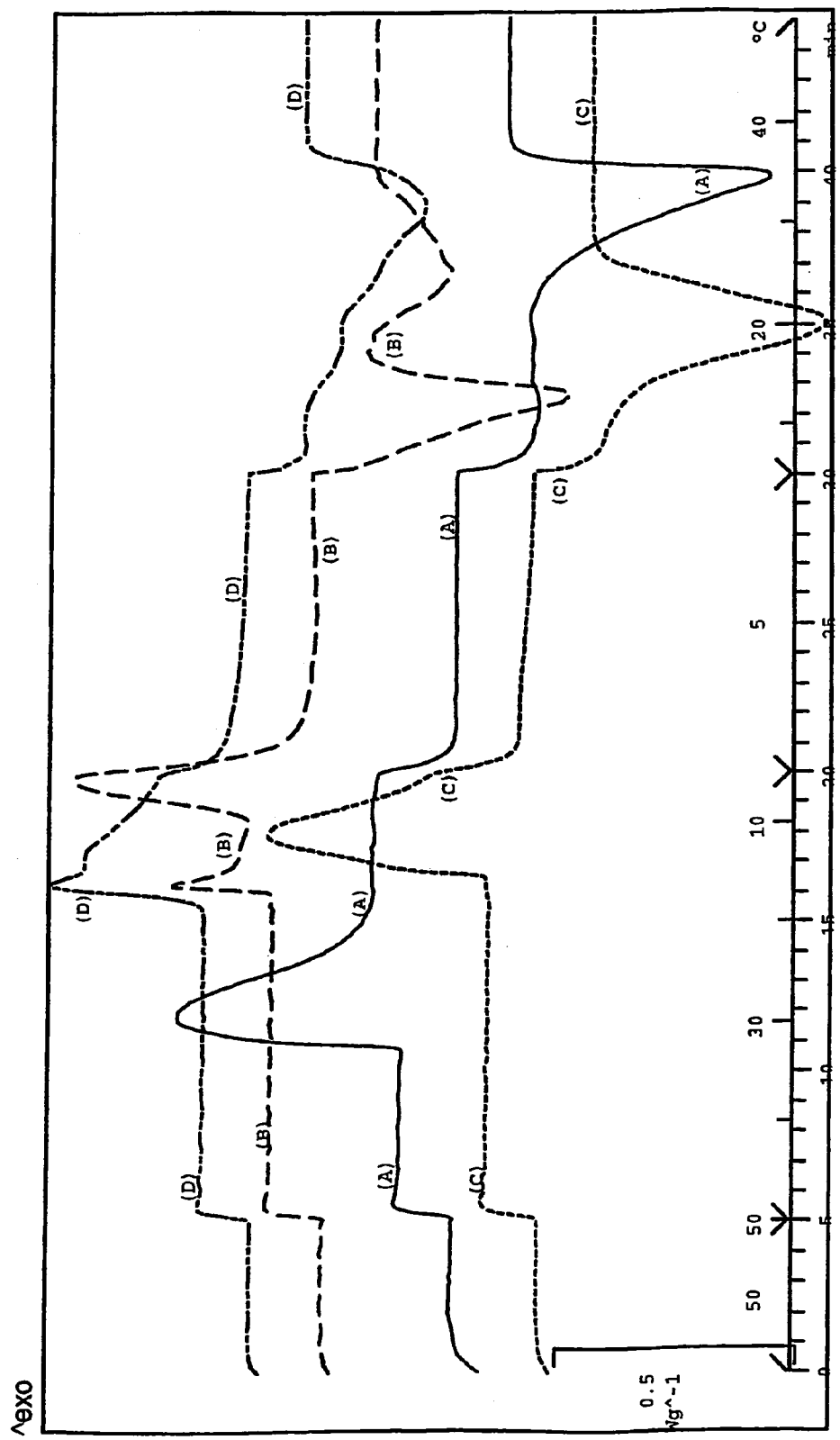

In FIG. 1 the solidification and melting behaviour is illustrated by applying Differential Scanning Calorimetry (DSC). The measurements were performed in a Mettler Toledo Star System apparatus using the following T-regime: Isotherm at 50° C. for 1 minute, cooling at a rate of 3° C./min, isotherm at 5° C. for 10 minutes followed by heating at a rate of 3° C./min to a final temperature of 50° C. The bracket to the left denotes an effect of 0.5 $Wg^{-1}$.

In FIG. 2 the melting behaviour when heating at a rate of 3° C./min to a final temperature of 50° C. after keeping the fats at 5° C. for 10 minutes (FIG. 2-1, representing the right portion of FIG. 1) vs. after keeping the fats at 20° C. for 72 hours (FIG. 2-2) is illustrated. The brackets to the left denote an effect of 0.5 Wg⁻.

The results of the DSC measurements are summarised in the following:

FIG. 1 shows the rapid crystallisation of a fat composition of the invention, and that the solidification/melting profile resembles that of a trans-hydrogenated fat. The reference non-temper Fat B appears to be a composite fat having two peaks of solidification and melting.

FIGS. 2-1 and 2-2 show that a fat composition of the invention and the trans-hydrogenated fat crystallises in a stable form. After a time delay of 72 hours the two other fats have re-crystallised into a more stable form as indicated by a shift of the melting peak towards a higher temperature.

Figure 3:
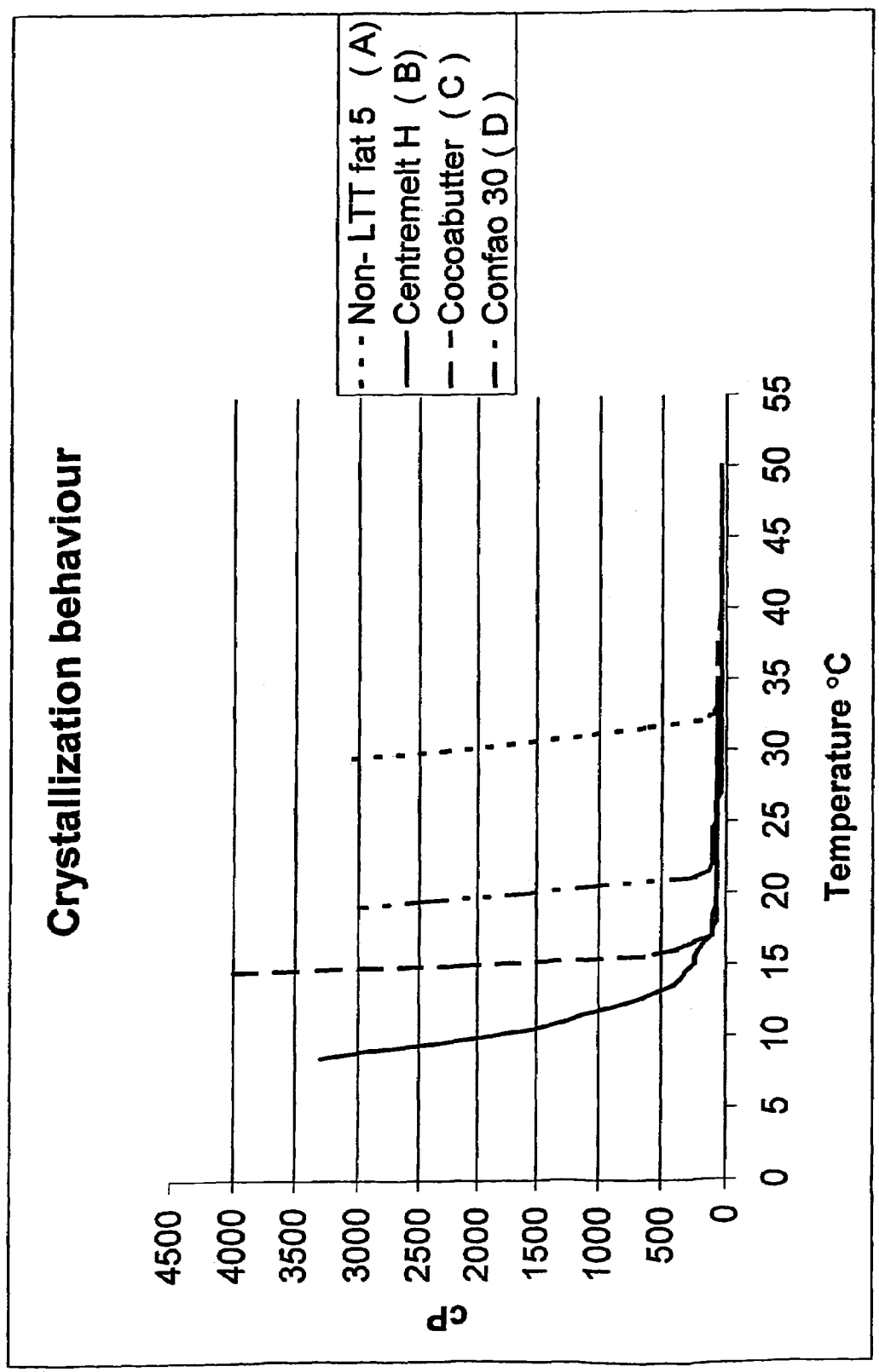

In FIG. 3 the onset and rate of crystallisation is illustrated by applying temperature controlled viscosimetric measurements. The measurements were performed in a Brookfield DV-III Rheometer fitted with a small sample adapter and spindle SC4-27, using the following T-regime: Isotherm at 50° C. for 10 minutes followed by cooling at a rate of 1° C./min.

The results are summarised in the following:

FIG. 3 shows that a fat of the invention has a fast crystallisation i.e. crystallisation onset at a relatively high temperature. Furthermore, the rate of crystallisation is comparable to that of a trans-hydrogenated fat.

DETAILED DESCRIPTION OF THE INVENTION

We have found that non-lauric, non-trans and non-temper fat compositions of the invention (in the following termed Non-LTT fats) can be obtained by fractionation of randomised triglyceride mixtures containing $C_{16}$-$C_{22}$ saturated fatty acids and as unsaturated fatty acids $C_{18:1}$ and $C_{18:2}$.

The starting TAG mixtures generally have the following fatty acid composition:

| | |
|---|---|
| total content of palmitic (C16:0), stearic (C18:0), oleic (C18:1) and linoleic (C18:2) acids: | 50-97% by weight, |
| total content of palmitic (C16:0) and stearic (C18:0) acids: | 25-60% by weight, |
| total content of arachidic (C20:0) and behenic (C22:0) acids: | 3-40% by weight, |
| total content of other fatty acids: | max. 10% by weight. |

To be called non-lauric the starting triglyceride mixtures and, thus, the fat compositions prepared from them according to the invention should contain less than 4% by weight of lauric acid, and it is desirable that their lauric acid content is max. 1% by weight, preferably max. 0.5% by weight. Similarly, to be called non-trans the starting triglyceride mixtures and, thus, the fat compositions prepared from them according to the invention should contain less than 3% by weight of trans-fatty acids, and it is desirable that their total content of trans-fatty acids is max. 1% by weight.

Normally the starting triglyceride mixtures will contain diglycerides, typically in the range of 3-8% by weight.

The starting TAG mixture can be obtained in many ways, e.g. by esterification of fatty acids or their esters of monovalent alcohols with glycerol, interesterification between a fat and free fatty acids or their esters, e.g. methyl esters, etc. Another method is to mix natural occurring triglycerides, fully hydrogenated triglycerides and/or fractions of oils and fats. The fatty material may be of animal or vegetable origin. We prefer that the component TAGs in the starting triglyceride mixture are of vegetable origin, e.g. palm oil, sunflower seed oil, high erucic rapeseed oil, etc.

Randomisation of the starting TAG mixture refers to a random distribution of the fatty acids on the glycerol molecules. This can be done by a transesterification process using a catalyst, e.g. sodium methoxide, enzymes, etc. The randomisation modifies the characteristics of the fat without chemically modifying the individual fatty acid composition of the mixture. The triglyceride mixture resulting from the rearrangement of the six basic fatty acids in the starting TAG mixture will contain up to 126 different TAGs not accounting for enantiomers. Each individual TAG has a specific melting point. A consequence of the increased number of different TAGs in the mixture is a change in the melting behaviour of the fat composition.

To tailor the melting and solidification characteristics of the fat composition to specific applications and to provide the fat compositions of the invention, it is necessary to remove unwanted fractions. Such fractions can be removed by known fractionation methods such as pressurised filtration fractionation (dry fractionation) or solvent fractionation e.g. as described in Bailey's Industrial Oils and Fat Products, Wiley-Interscience Publication, Fourth Edition (1985), Vol. 3, p. 1-39. In fractionation, the composition is modified by a selective physical separation of the different component groups. It is basically a thermo-mechanical separation process in which a multi-component mixture is physically separated into two or more fractions with distinct physical and chemical properties.

The final concentration of diglycerides in the fat composition is dependent upon the concentration in the starting triglyceride mixture, the type and amount of catalyst used in the transesterification process and the technical details in the fractionation step. Thus, in the fat compositions according to the invention the content of diglycerides generally is max. 10% by weight, preferably max. 5% by weight.

The procedures involved in providing the constituent triglycerides in the starting TAG mixture, randomisation and fractionation are known in the art. But it is surprising that selected fractions of a randomised, well-defined triglyceride mixture comprising palmitic, stearic, arachidic, behenic, oleic and linoleic fatty acids as constituents possess the following properties: Non-temper, rapid nucleation and high rate of crystallisation, anti-bloom and soft melting characteristics. The soft melting properties are quite unexpected in fat compositions with such a high content of high-melting, saturated fatty acids. Furthermore, it is surprising that all the above-mentioned properties are preserved when considerable amounts of other oils and fats are added. All in all, the number of combined features of the fat compositions of the invention is surprising and not obvious to a person skilled in the art, and an explanation would be speculative at this stage.

The characteristics of said selected fractions will be detailed in the following.

The selected fractions of the invention can be obtained by removing the high melting TAGs or, in another aspect, the high melting and the low melting TAGs resulting in a mid-fraction. The Non-LTT fat compositions of the invention so obtained have the following physical and chemical properties:

1. Slip melting point measured according to AOCS Cc 3-25: below 36° C. and solid fat content (SFC) measured according to IUPAC 2.150 mod. (stabilised at 20° C. for 24 h): above 25% by weight at 20° C.
2. Total content of saturated fatty acids measured according to IUPAC 2.301 and 2.304: 40-75% by weight, preferably 45-70% by weight.
3. Total content of arachidic and behenic acids: 340% by weight, preferably 5-35% by weight, and total content of palmitic and stearic acids: 25-60% by weight, preferably 25-50% by weight, both measured according to IUPAC 2.301 and 2.304.
4. Total content of triglycerides having triglyceride composition (TGC) of C56-C60 measured by number of total carbon atoms of constituent fatty acids according to IUPAC 2.323: min. 9% by weight, preferably min. 15% by weight.
5. Total content of $S_2U$-type triglycerides: min. 25% by weight, preferably min. 35% by weight, where S=saturated fatty acids and U=unsaturated fatty acids.

The melting behaviour of the Non-LTT fat is tailored to the application in question. Fat compositions for compound coatings have a high solid fat content (SFC) at room temperature e.g. >70% SFC at 20° C., <15% SFC at 35° C. Fat compositions for fillings are more soft e.g. >25% SFC at 20° C., <10% SFC at 35° C.

The Non-LTT fat compositions of the invention usually have an onset of crystallisation in the temperature range of 36-22° C. and crystallize in a stable form.

The above mentioned DSC values refer to measurements performed in a Mettler Toledo Star System using the following T-regime: Isotherm at 50° C. for 1 minute, cooling at a rate of 3° C./min.

In dynamic, temperature controlled rheological measurements the Non-LTT fat compositions according to the invention displayed an onset of crystallisation at relatively high temperatures and a crystallisation rate comparable to that of trans-hydrogenated fats (Example 2).

The Non-LTT fat compositions according to the invention have a high compatibility with other oils and fats as well as other food ingredients e.g. sugar, milk powder and cocoa powder, etc. This, combined with their melting behaviour, makes them useful as a component of oils and fats which are to be incorporated in food products for humans and other mammals such as hardstock in margarine oils. It also makes them useful as ingredients in confectionery, bakery and dairy fillings, e.g. in concentrations of 5-60% by weight (Example 3), wherein they also exhibit good aerating properties (Examples 6 and 7), and in confectionery coating compounds, chocolate-like products etc., e.g. in concentrations of 1-55% by weight, preferably 140% by weight (Example 4).

The Non-LTT fat compositions according to the invention possess anti-bloom properties when added to chocolate and chocolate-like products in low concentrations, e.g. 0.5-10% by weight, preferably 1-5% by weight (Example 5).

The Non-LTT fat compositions according to the invention also exhibit activity as aerating boosters in combination with commercial filling fats in concentrations of min. 1% by weight, preferably 2-10% by weight (Example 6-B).

The Non-LTT fat compositions according to the invention further exhibit superior barrier properties when used as a water barrier in applications where materials with high and low humidity are in direct contact (Example 9).

Furthermore, the Non-LTT fats according to the invention are useful as emollients, excipients and consistency giving ingredients in cosmetics, pharmaceuticals or pharma-like (OTC, over the counter) products, e.g. emulsions, ointments, lip balm, suppositories, etc. (Example 10).

The invention will be better understood with reference to the following examples that are illustrative and should not be taken as limiting the scope of the present invention as described in the claims.

EXAMPLES

Example 1

Composition and Characteristics of Non-LTT Fats

The starting oil mixtures are shown in the following table:

| Product/Parameter | No. 1 | No. 2 | No. 3 | No. 4 | No. 5 | No. 6 |
|---|---|---|---|---|---|---|
| Composition, %: | | | | | | |
| 1. FH, high erucic rapeseed oil | 52 | 29 | 13 | 40 | 65 | 26 |
| 2. FH, rapeseed oil | 0 | 14 | 24 | 0 | 0 | 0 |
| 3. Palm oil, F-57 | 0 | 57 | 63 | 60 | 0 | 0 |
| 4. Palm oil, F-67 | 48 | 0 | 0 | 0 | 0 | 37 |
| 6. High oleic sunflower oil | 0 | 0 | 0 | 0 | 35 | 37 |
| Fatty acid composition, %: | | | | | | |
| C12:0 | 0.3 | 0.2 | 0.2 | 0.2 | 0.2 | 0.3 |
| C14:0 | 0.6 | 0.7 | 0.7 | 0.7 | 0.2 | 0.4 |
| C16:0 | 18.3 | 25.8 | 27.3 | 28.2 | 5.6 | 15.1 |
| C18:0 | 21.9 | 26.1 | 29.6 | 19.0 | 26.6 | 12.6 |
| C18:1 | 23.3 | 24.3 | 26.6 | 23.1 | 29.0 | 47.9 |
| C18:2 | 6.7 | 6.4 | 7.1 | 5.9 | 3.6 | 8.6 |
| C20:0 | 4.9 | 3.1 | 2.0 | 4.0 | 5.9 | 2.6 |
| C22:0 | 22.9 | 12.6 | 6.1 | 17.8 | 27.7 | 11.6 |
| Others | 1.1 | 0.8 | 0.4 | 1.1 | 1.2 | 0.9 |
| Total trans content | 0.3 | 0.2 | 0.3 | 0.4 | 0.0 | 0.4 |

Note:
FH, denotes "fully hydrogenated".
The suffix F refer to various fractions and the numbers to the typical iodine value.

The starting oil mixtures were randomised in a standard interesterification process performed for 30 minutes at 90-100° C. with sodium methoxide as catalyst.

The randomised triglyceride mixtures were fractionated as illustrated in the following:

Each of the triglyceride mixtures nos. 1-5 was mixed with 6 parts of hexane, heated to 25-30° C. and cooled to 3° C. The precipitated high melting fraction was filtered off and the filtrate cooled to a second fractionation temperature of −16° C. The precipitated mid-fraction was filtered off, washed with hexane and desolventised. The yield was in the range of 30-40% by weight.

Triglyceride mixture no. 6 was dry-fractionated at a temperature of 32° C. to remove the high melting fraction. The lower melting fraction was obtained in a yield of 31% by weight.

All the selected fractions so obtained were bleached and deodorised by standard procedures known in the art.

The resulting oil fractions have the following characteristics:

| Product/Parameter | No. 1 | No. 2 | No. 3 | No. 4 | No. 5 | No. 6 |
|---|---|---|---|---|---|---|
| Fatty acid composition in %: | | | | | | |
| C12:0 | 0.3 | 0.2 | 0.2 | 0.2 | 0.1 | 0.2 |
| C14:0 | 0.5 | 0.5 | 0.5 | 0.5 | 0.1 | 0.4 |
| C16:0 | 14.8 | 22.0 | 25.3 | 22.8 | 5.3 | 14.5 |
| C18:0 | 21.1 | 26.3 | 30.8 | 18.9 | 27.5 | 13.2 |

-continued

| Product/Parameter | No. 1 | No. 2 | No. 3 | No. 4 | No. 5 | No. 6 |
|---|---|---|---|---|---|---|
| C18:1 | 23.6 | 26.5 | 27.4 | 25.3 | 29.0 | 45.4 |
| C18:2 | 6.9 | 6.5 | 6.5 | 6.3 | 3.3 | 8.0 |
| C20:0 | 5.3 | 3.3 | 2.1 | 4.4 | 6.1 | 2.9 |
| C22:0 | 26.0 | 13.7 | 6.4 | 20.7 | 27.5 | 13.9 |
| Others | 1.5 | 1.0 | 0.8 | 0.9 | 1.1 | 1.5 |
| Total trans content | 0.4 | 0.9 | 0.3 | 0.5 | 0.0 | 0.4 |
| Triglyceride composition (TGC) in %: | | | | | | |
| C50 | 4.7 | 11.5 | 14.7 | 10.4 | 1.3 | 9.5 |
| C52 | 13.7 | 27.8 | 36.4 | 19.5 | 5.6 | 32.2 |
| C54 | 15.4 | 20.8 | 25.0 | 14.4 | 19.1 | 0.1 |
| C56 | 22.4 | 16.4 | 9.7 | 23.7 | 16.0 | 17.9 |
| C58 | 24.6 | 14.2 | 8.2 | 16.7 | 37.5 | 24.9 |
| C60 | 5.3 | 2.0 | 0.9 | 3.6 | 7.0 | 3.5 |
| C62 | 9.4 | 2.5 | 0.7 | 5.8 | 10.0 | 4.8 |
| Others | 4.5 | 4.8 | 4.4 | 5.9 | 3.5 | 7.1 |
| SFC in % at ° C.: | | | | | | |
| 20 | 79.8 | 84.3 | 84.7 | 85.6 | 71.3 | 28.0 |
| 25 | 78.1 | 69.6 | 68.5 | 77.8 | 67.1 | 20.4 |
| 30 | 54.0 | 19.0 | 15.5 | 36.7 | 59.2 | 8.7 |
| 35 | 3.6 | 0.0 | 0.0 | 0.0 | 4.2 | 2.2 |
| Slip melting point ° C. | 34.1 | 31.8 | 31.7 | 32.9 | 35.2 | 33.9 |
| Solidification/melting by DSC in ° C.: | | | | | | |
| Solidification onset | 34.2 | 26.3 | 23.5 | 30.8 | 33.0 | 25.1 |
| Solidification peak max. | 29.2 | 22.6 | 21.3 | 25.1 | 30.7 | 24.0 |
| Melting peak maximum | 32.2 | 29.6 | 29.4 | 30.1 | 33.3 | 30.1 |

Note:
Slip melting points were measured according to AOCS Cc 3-25. DSC measurements were performed in a Mettler Toledo Star System using the following T-regime: Isotherm at 50° C. for 1 minute, cooling at a rate of 3° C./min to 5° C. The samples were conditioned in the test pans for 72 hours at 20° C., transferred to the DSC instrument and kept isothermal at 20° C. for 1 minute followed by heating at a rate of 3° C./min to reach a final temperature of 50° C.

Example 2

Crystallisation Characteristics of Non-LTT Fats in Comparison with Commercially Available Temper and Non-temper Fats The crystallisation characteristics of Non-LTT fats were compared with the following commercial available fats:
1. Cocoa Butter (West Africa) is a temper fat.
2. "Confao 30" (Aarhus Oliefabrik A/S) is a non-temper filling fat based on trans-hydrogenated oils of non-lauric origin.
3. "Centremelt H" (Loders Croklaan. B. V.) is a non-lauric, non-trans and non-temper filling fat.

The test methods used were as described in the following:
1. Onset of solidification by DSC:

Automatic solidification onset temperature measurements were performed in a Mettler Toledo Star System using the following T-regime: Isotherm at 50° C. for 1 minute, cooling at a rate of 3° C./min to 5° C.

2. Onset of Crystallisation and Rate of Crystallisation by Viscosimetric Measurements:

The measurements were performed in a Brookfield DV-III Rheometer fitted with a small sample adapter and spindle SC4-27, using the following T-regime: Isotherm at 50° C. for 10 minutes followed by cooling at a rate of 1° C./min.

The onset temperature is determined as the projection of the intersection point of the tangents to the viscosity curve on the T-axis.

The crystallisation rate is calculated as the viscosity increase from onset temperature and three degrees lower, divided by three.

The results are tabulated in the following:

| Product/Parameter | DSC onset temperature in ° C. | Viscosimetric onset temperature in ° C. | Crystallisation rate as ΔcP/° C. |
|---|---|---|---|
| Cocoa Butter | 15.8 | 15.6 | 3512 |
| "Confao 30" | 18.1 | 20.9 | 1413 |
| "Centremelt H" | 17.3/9.8 | 13.1 | 465 |
| Non-LTT fat no. 1 | 34.2 | 31.1 | 703 |
| Non-LTT fat no. 2 | 26.3 | 25.3 | 1262 |
| Non-LTT fat no. 3 | 23.5 | 22.2 | 1705 |
| Non-LTT fat no. 4 | 30.8 | 29.1 | 793 |
| Non-LTT fat no. 5 | 33.0 | 32.2 | 1072 |
| Non-LTT fat no. 6 | 25.1 | 24.7 | 599 |

The results show that there is a good correlation between the onset temperature values measured by the viscosimetric method and by DSC.

Furthermore, the onset temperature for the Non-LTT fats is considerably higher than the measured values for the reference fats. This in combination with the high crystallisation rate gives the Non-LTT fats a rapid solidification that is useful in industrial applications.

Example 3

Use of a Non-LTT Fat in Confectionery Fillings

Non-LTT fat no. 1 from Example I was tested in the following filling compositions:

| Product/Parameter | Comp. #1 | Comp. #2 | Comp. #3 | Comp. #4 |
|---|---|---|---|---|
| Ingredients: | | | | |
| Sugar | 40 | 32.8 | 38 | 37 |
| Yoghurt Powder | 15 | 0 | 0 | 0 |
| Non-LTT Fat | 35 | 26 | 26 | 32 |
| Cocoa Mass | 0 | 6.7 | 0 | 0 |
| Cocoa Butter | 0 | 8 | 0 | 0 |
| Cocoa Powder | 0 | 0 | 4 | 8 |
| Whole Milk Powder | 10 | 8.4 | 10 | 8 |
| Skim Milk Powder | 0 | 2.1 | 0 | 3 |
| Hazelnut Paste | 0 | 16 | 22 | 12 |
| Total Fat Content in %: | 37.6 | 49.5 | 42.2 | 42.2 |
| Fat Composition in % relative: | | | | |
| Non-LTT Fat | 93.1 | 52.5 | 61.6 | 75.8 |
| Cocoa Butter | 0 | 24.0 | 1.0 | 2.2 |
| Milk Fat | 6.9 | 4.0 | 6.1 | 4.9 |
| Hazelnut Oil | 0 | 19.5 | 31.3 | 17.1 |

The four compositions were prepared in a Hobart mixer at 50° C. The resulting mass was refined in a Lehmann three-roll refiner to a particle size of 20-25 μm. After this the products were conched in a Hobart machine for two hours and finally added 0.4% by weight lecithin and 0.05% by weight vanillin.

At 30° C. the fillings were transferred to chocolate shells and cooled in a Blummen three-stage, cooling tunnel. The temperature settings were 12° C. in the first zone, 6° C. in the second zone and 12-14° C. in the final zone. The total cooling time was 20 minutes.

The fillings were evaluated immediately and after a six months storage period. In a sensory test performed by a trained test panel all the products passed. There were no sign of sandiness or visible crystal agglomeration before or after the storage period. These findings were confirmed by DSC, melting point, pulsed-NMR and texture measurements before and after the storage period.

This example demonstrates the compatibility with other ingredients and that the non-temper feature is preserved in fat mixtures with a high content of tri-unsaturated triglycerides.

Example 4

Use of a Non-LTT Fat in Confectionery Coatings

Non-LTT fat no. 1 from Example 1 was tested in the following compound coating compositions:

| Product/Parameter | Compound #1 | Compound #2 |
|---|---|---|
| Ingredients in %: | | |
| Sugar | 49 | 49 |
| Cocoa Powder | 15 | 15 |
| Non-LTT Fat | 30 | 24 |
| Cocoa Butter | 0 | 6 |
| Skim Milk Powder | 6 | 6 |
| Total Fat Content in %: | 31.7 | 31.7 |
| Fat Composition in % rel.: | | |
| Cocoa Butter | 5.4 | 24.3 |
| Non-LTT Fat | 94.6 | 75.7 |

The two compositions were mixed in a melangeur at 60° C. for 15 minutes. The resulting mass was refined in a Lehmann three-roll refiner to a particle size of 20-25 μm. After this the products were conched in a Hobart machine for six hours at 60° C. and finally 0.4% by weight lecithin and 0.05% by weight vanillin was added.

The compounds were transferred to a Nielsen Baby Flex enrober and were at 40-42° C. used to coat spun-cakes followed by cooling in a Blummen three-stage cooling tunnel. The temperature settings were 5-6° C. in the first two zones and 12-14° C. in the final zone. The total cooling time was 5 minutes.

The coatings were evaluated immediately and after an eight months storage period by a trained test panel. The products passed the sensory test and after the storage period they still had a nice gloss and there was no sign of fat-bloom. The storage stability was confirmed by DSC and texture measurements.

In conclusion the Non-LTT fat has a good compatibility and stability over time with cocoa butter and performed just as well as non-lauric CBSs with a high content of trans fatty acids.

Example 5

Non-LTT Fats Used as Anti-Bloom Agent

Non-LTT fats no. 1 and no. 5 from Example 1 were tested as anti-bloom agents in the following milk chocolate and dark chocolate bar formulations:

| Composition/Ingredients in %: | Dark Comp. #1 | Dark Comp. #2 | Dark Comp. #3 | Dark Comp. #4 | Milk Comp. #1 | Milk Comp. #2 | Milk Comp. #3 |
|---|---|---|---|---|---|---|---|
| Cocoa Mass | 40 | 40 | 40 | 40 | 16 | 16 | 16 |
| Cocoa Butter | 10 | 7 | 9 | 7 | 19 | 16 | 16 |
| Sugar | 50 | 50 | 50 | 50 | 40 | 40 | 40 |
| Milk Fat | 0 | 3 | 0 | 0 | 0 | 3 | 0 |
| Whole Milk Powder | 0 | 0 | 0 | 0 | 20 | 20 | 20 |
| Skim Milk Powder | 0 | 0 | 0 | 0 | 5 | 5 | 5 |
| Non-LTT Fat no. 1 | 0 | 0 | 0 | 0 | 0 | 0 | 3 |
| Non-LTT Fat no. 5 | 0 | 0 | 1 | 3 | 0 | 0 | 0 |

The ingredients were mixed in a melangeur at 60° C. for 15 minutes. The resulting mass was refined in a Lehmann three-roll refiner to a particle size of 20-25 μm. After this the products were conched in a Hobart machine for sixteen hours at 60° C. and finally 0.4% by weight lecithin and 0.05% by weight vanillin were added.

Before depositing the chocolate mass into 100 g moulds, it was tempered in an Aasted AMT 10 mini tempering machine and the quality of the tempering procedure verified by means of an Exotherm 7400 tempermeter. The chocolate was cooled in the moulds in a Blummen three-stage cooling tunnel. The temperature settings were 10-12° C. in the first zone, 5-6° C. in the second zone and 14-15° C. in the final zone. The total cooling time was 30 minutes. The chocolate bars were conditioned at 20° C. for three days before the bloom test was started.

In isotherm reference test at 20° C. none of the compositions showed any sign of fat-bloom after ten weeks of storage.

An accelerated test was performed in a Termaks cycle cabinet. Each cycle involves heating at 31° C. for six hours and cooling at 21° C. for six hours. Fat-bloom occurrence was evaluated by visual observation.

The results are tabulated in the following:

| Storage Time in Weeks | Dark Comp. #1 | Dark Comp. #2 | Dark Comp. #3 | Dark Comp. #4 | Milk Comp. #1 | Milk Comp. #2 | Milk Comp. #3 |
|---|---|---|---|---|---|---|---|
| 1 | − | − | − | − | − | − | − |
| 2 | − | − | − | − | − | − | − |
| 3 | + | − | − | − | − | − | − |
| 4 | ++ | + | + | − | + | − | − |
| 5 | +++ | ++ | + | − | + | + | − |
| 6 | +++ | +++ | ++ | − | ++ | + | − |
| 7 | +++ | +++ | ++ | − | ++ | + | − |
| 8 | +++ | +++ | +++ | − | ++ | ++ | − |
| 9 | +++ | +++ | +++ | − | +++ | +++ | − |
| 10 | +++ | +++ | +++ | − | +++ | +++ | − |

Legend:
− = nice gloss, no bloom;
+ = bad gloss, weak bloom;
++ = bloom;
+++ = strong bloom.

From the results it can be seen that an addition of 1% by weight Non-LTT fat to dark chocolate has an anti-bloom effect comparable to an addition of 3% by weight milk fat.

In both types of chocolate no fat-bloom was observed in the test when 3% by weight of Non-LTT fat was added to the compositions.

Example 6

Use of Non-LTT Fat in Aerated Fillings

The aerating properties of a Non-LTT fat was tested in the following typical filling formulations by open bowl whipping at normal pressure.

A. Nougat Filling Composition

The test composition and a reference were prepared in a Hobart N-50 mixer, speed 1 at 50° C. The resulting mass was refined in a Lehmann three-roll refiner to a particle size of 20-25 μm. After this the products were conched for two hours at 50° C., and finally 0.4% of lecithin and 0.05% vanillin was added.

The density of the resulting products was measured before and after whipping in a Hobart N-50 mixer at speed 2 for 5 minutes at 20° C.

The compositions and results are tabulated in the following:

| Product/Parameter | Test Composition | Reference |
|---|---|---|
| Ingredients: | | |
| Sugar | 38 | 38 |
| Non-LTT Fat[1] | 26 | 0 |
| Confao 5[2] | 0 | 26 |
| Hazelnut Paste | 22 | 22 |
| Whole Milk Powder | 10 | 10 |
| Cocoa Powder | 4 | 4 |
| Results: | | |
| Density before whipping | 1.15 | 1.15 |
| Density after whipping | 0.50 | 0.70 |
| Overrun in % | 130 | 64 |

[1]Mixture of 50% No. 4 and 50% No. 6
[2]A traditional trans-hydrogenated filling fat from Aarhus Oliefabrik A/S B. Biscuit Filling Composition The test composition and a reference were prepared by mixing the ingredients in a Hobart N-50 mixer at speed 1 for 15 minutes at 40° C.

The density of the resulting products was measured before and after whipping in a Hobart N-50 mixer at speed 2 for 5 minutes at 10° C.

The compositions and results are tabulated in the following:

| Product/Parameter | Test Composition | Reference |
|---|---|---|
| Ingredients: | | |
| Icing Sugar | 60 | 60 |
| Non-LTT Fat[1] | 2 | 0 |
| Palm Mid Fraction | 38 | 40 |
| Results: | | |
| Density before whipping | 1.18 | 1.18 |
| Density after whipping | 0.62 | 0.92 |
| Overrun in % | 90 | 28 |

[1]Mixture of 50% No. 4 and 50% No. 6

C. Filling Composition Containing Water and Emulsifier

The test composition and a reference were prepared by mixing the fat and emulsifier at 0.50° C. The mixture was allowed to pre-crystallise for 45 minutes at 15° C. During whipping in a Hobart N-50 mixer at speed 3 the glucose syrup was added. After 3 minutes of whipping at 20° C. the density was measured.

The density before whipping was measured on a mixture of gently mixed fat and glucose syrup.

The compositions and results are tabulated in the following:

| Product/Parameter | Test Composition | Reference |
|---|---|---|
| Ingredients: | | |
| Non-LTT Fat[1] | 40 | 0 |
| Confao 12[2] | 0 | 40 |
| Emulsifier | 1 | 1 |
| Glucose Syrup 72% DS | 59 | 59 |

-continued

| Product/Parameter | Test Composition | Reference |
|---|---|---|
| Results: | | |
| Density before whipping | 1.12 | 1.12 |
| Density after whipping | 0.48 | 0.81 |
| Overrun in % | 133 | 38 |

¹Mixture of 40% No. 4 and 60% No. 6
²A traditional trans-hydrogenated filling fat ex. Aarhus Oliefabrik A/S From the abovementioned examples it appears that the Non-LTT fat improve the overrun by a factor of 2 to 3 and when used as an additive it acts as an aerating booster.

Example 7

Use of Non-LTT Fats in Pressure Aerated Fillings

This example illustrates the excellent aerating properties of Non-LTT fats vs. commercial filling fats by a pressurized whipping process.

Test Materials

Four fillings each containing 50% of a filling fat were made up according to the following recipe:

| | | |
|---|---|---|
| Cocoa Powder | 10% | |
| Icing Sugar | 40% | |
| Filling Fat | 50% | |

The following filling fats were used:

Confao 5, a traditional trans-hydrogenated filling fat of medium hardness

Confao 22, a traditional trans-hydrogenated filling fat of a soft type.

Non-LTT no. 4, a fat of the invention, hard type.

Non-LTT no. 6, a fat of the invention, soft type.

Test Method

The ingredients were mixed in a Hobart N-50 mixer at 40° C. for 15 minutes.

The resulting product was transferred to the inlet tank of a Pilot Mondomixer, type UA-05 and pressure aerated at the following parameters:

| | |
|---|---|
| Product Flow | 0.110 kg/min |
| Nitrogen Flow | 0.50 l/min |
| Mixer Speed | 300 RPM |
| Pressure | 4.5 bar |
| Cooling Water Temp. | 5-6° C. |
| Product Inlet Temp. | 28° C. |
| Product Outlet Temp. | 25° C. |

Results

All the test products had a density of 1.160 before whipping.

The density after aeration and the calculated overrun are tabulated in the following:

| Product/Parameter | Density after Aeration | Overrun in % |
|---|---|---|
| Confao 22 | 0.515 | 125 |
| Confao 5 | 0.620 | 87 |
| Non-LTT, no. 4 | 0.230 | 404 |
| Non-LTT, no. 6 | 0.232 | 400 |

Example 8

Chocolate-Softening Properties of Non-LTT Fat in Fillings

It is well known that chocolate fillings tend to soften the embedding chocolate shell.

Normally, there is a relationship between the softening effect and the triglyceride composition of the filling fat. Milk fat, lauric fat, hazelnut oil and trans-hydrogenated oils migrate and soften the chocolate whereas CBE-type fats, that resembles the triglyceride composition of cocoa butter, migrate and soften much less.

The triglyceride composition of Non-LTT fat is very different to that of cocoa butter. Consequently, Non-LTT fat is expected to have a high degree of softening effect. Surprisingly, this is not the case as demonstrated by the following test.

Test Materials

Five nougat fillings each containing 26% of a filling fat were made according to the formulation in example 6 under heading A.

The following filling fats were used:

Confao 5, a traditional trans-hydrogenated filling fat of medium hardness.

Confao BR 5, a bloom retarding, interesterified filling fat of medium hardness.

Confao BR 30, a bloom retarding, interesterified filling fat, hard type.

Non-LTT fat of medium hardness (mixture of 30% No. 4 and 70% No 6).

Non-LTT fat, hard type (mixture of 70% No. 4 and 30% No. 6).

The chocolate used in the test had the following composition:

| | |
|---|---|
| Cocoa Mass | 40.0% |
| Cocoa Butter | 9.6% |
| Sugar | 50.0% |
| Lecithin | 0.4% |

The chocolate and the fillings were mixed and refined as described under heading A in example 1x. After this the products were conched for six hours at 50° C.

Test Method

The samples were prepared as described in the following:

Four ml of tempered chocolate was moulded in a conic, stainless steel cylinder (inner diameter 27 mm/29 mm) and cooled for five minutes in a cooling tunnel at 10° C. Six ml of nougat filling at 30° C. was moulded on top of the chocolate. The mould was passed through a cooling tunnel with the following stages: 10 min at 10° C., 10 min at 5° C. and 10 min at 14° C. After this the sample was pressed out of the mould and put on store for three days, one month and three months respectively at 20° C.

The samples were measured using the following procedure:

Before measurement the sample was cooled at 5° C. for 24 hours and the filling removed from the chocolate. The chocolate part was left at 20° C. for 24 hours before texture measurement was performed in a Texture Analyser Xt2-i set to penetrate 2 mm.

Results

The tabulated results are mean values of five measurements of the penetration force expressed in grams:

| Filling Fat/Storage Time | Three Days | One Month | Three Months |
|---|---|---|---|
| None, reference | 696 | — | — |
| Confao 5 | — | 558 | 361 |
| Confao BR 5 | — | 557 | 305 |
| Confao BR 30 | — | 564 | 338 |
| Non-LTT, medium | — | 568 | 451 |
| Non-LTT, hard | — | 578 | 462 |

From the results it appears that fat from the filling migrates into the chocolate and softens it. After one month of storage all filling fats perform almost identical. After three months of storage the Non-LTT fats perform better than ordinary fats.

Example 9

Barrier Properties of Non-LTT Fat

Edible fats are used to form a water barrier in applications where materials with high and low humidity are in direct contact. Typical examples include biscuit and wafers with a layer of caramel or marmalade and wrapping paper for candies.

The barrier properties of Non-LTT fat were compared with these of Barrier Fat 76 ex. Aarhus Oliefabrik A/S. Barrier Fat 76 is a non-lauric, non-temper barrier fat of proven quality in practical applications.

Test Method

The permeability of water vapour through a membrane coated with a 125-130µ film of fat was measured according to the following procedure:

Ten grams of dry silica gel was weighed into a polypropylene beaker (Ø=40 mm, H=47 mm) and sealed with a membrane of filter paper (Whatman no. 1, Ø=42 mm). On the surface of the membrane 20-30 spots of liquid fat at 50° C. was applied in a total amount of 0.160±0.005 g. Following this the test module was vibrated in order to distribute the fat. To secure a uniform film of fat the test module was placed in a heating cabinet at 70° C. for half an hour and vibrated before cooling at 10° C. for ten minutes. After this the initial weight of the test module was determined (time zero).

After a challenge period of one week at 20° C. and 50-55% relative humidity the weight gain of each test module was recorded and the moisture transfer calculated.

Results

The tabulated values for the fats are mean values of eight single determinations.

The calculated standard deviation was ±0.01 g/m$^2$/h.

| Product/Parameter | Weight Gain in mg per Hour | Water Permeability in g/m$^2$ per Hour |
|---|---|---|
| Reference without fat | 13.37 | 10.64 |
| Barrier Fat 76 | 0.70 | 0.56 |
| Non-LTT no. 4 | 0.46 | 0.37 |

The results show that the Non-LTT fat has superior barrier properties in comparison with an optimised commercial product.

Example 10

Use of a Non-LTT Fat in a Lip Balm Formulation

Non-LTT fat no. 4 from Example 1 was tested in the following lip balm formulation:

| Ingredient/ Trade Name | CTFA/INCI Name | Test Composition | Reference Composition |
|---|---|---|---|
| "Cegesoft PS-6" | Vegetable Oil | 8% by weight | 8% by weight |
| "Hyfatol 16-95" | Cetyl Alcohol | 13% by weight | 13% by weight |
| "Cremao CE-34" | Palm Glycerides | — | 6% by weight |
| Non-LTT Fat | — | 6% by weight | — |
| White Beeswax | Beeswax | 5% by weight | 5% by weight |
| "Rilanit IBO" | Butyl Oleate | 13% by weight | 13% by weight |
| White Vaseline | Petrolatum | 55% by weight | 55% by weight |

Note:
"Cegesoft" and "Rilanit" are trade names of Cognis Deutschland GmbH.
"Hyfatol" and "Cremao" are trade names of Aarhus Oliefabrik A/S.
"Cremao CE-34" is a CBE-type fat with a melting point of 34° C.

All the ingredients were heated to 75° C. and mixed. The mixture was filled into 5 ml tubes at 50° C. and cooled to room temperature.

The two lip balm sticks were tested by three skilled panellists. The two sticks performed well, but the test composition had a better gloss, and when applied to the skin the stick was more firm than the reference containing "Cremao CE-34".

This example demonstrates the compatibility of the Non-LTT fat with non-glyceridic ingredients normally used in cosmetic and pharmaceutical formulations.

The invention claimed is:

1. A non-lauric, non-trans, non-temper (Non-LLT) fat composition comprising a fraction obtained from a randomised triglyceride mixture in which min. 90% by weight of the constituent fatty acids are: palmitic (C16:0), stearic (C18:0), arachidic (C20:0), behenic (C22:0), oleic (C18:1) and linoleic (C18:2) acid and the total content of arachidic and behenic acid is 3-40% by weight and the total content of palmitic and stearic acids is 25-60% by weight, said fraction having the following physical and chemical properties:
    (1) slip melting point measured according to AOCS Cc 3-25: below 36° C. and solid fat content (SFC) measured according to IUPAC 2.150 mod. (stabilised at 20° C. for 24 h): above 25% by weight at 20° C.;
    (2) total content of saturated fatty acids measured according to IUPAC 2.301 and 2.304: 40-75% by weight;
    (3) total content of arachidic and behenic acids: 3-40% by weight, and total content of palmitic and stearic acids: 25-60% by weight, both measured according to IUPAC 2.301 and 2.304;

(4) total content of triglycerides having triglyceride composition (TGC) of C56-C60 measured by number of total carbon atoms of constituent fatty acids according to IUPAC 2.323: min. 9% by weight;

(5) total content of $S_2U$-type triglycerides: min. 25% by weight, where S=saturated fatty acids and U=unsaturated fatty acids.

2. A fat composition of claim 1 wherein the molar content of behenic acid is higher than that of arachidic acid.

3. A fat composition of claim 1 wherein the content of lauric acid is max. 1% by weight.

4. A fat composition of claim 1 wherein the total content of trans fatty acids is max. 1% by weight.

5. A fat composition of claim 1 wherein the content of diglycerides is max. 10% by weight.

6. A fat composition of claim 1 which is of vegetable origin.

7. A fat composition of claim 1 which by differential scanning calorimetry (DSC) performed in a Mettler Toledo Star System using the following T-regime: isotherm at 50° C. for 1 minute, cooling at a rate of 3° C./min, has an onset of crystallisation in the temperature range of 36-22° C. and crystallises in a stable form.

8. A food product for humans and other maminals comprising the fat composition of claim 1 as a component of oils and fats.

9. A confectionery, bakery or dairy filling comprising the fat composition of claim 1 as an ingredient in a concentration of 5-60% by weight.

10. A confectionery, bakery or dairy filling of claim 9, comprising the fat composition of claim 1 in a concentration of 10-50% by weight.

11. A confectionery coating compound comprising the fat composition of claim 1 as an ingredient in a concentration of 1-55% by weight.

12. A confectionery coating compound of claim 11, comprising the fat composition of claim 1 in a concentration of 1-40% by weight.

13. A chocolate or chocolate-like product comprising the fat composition of claim 1 as a bloom inhibitor in a concentration of 0.5-10% by weight.

14. A chocolate or chocolate-like product of claim 13, comprising the fat composition of claim 1 in a concentration of 1-5% by weight.

15. An aerated confectionery product, bakery product or dairy fillings comprising the fat composition of claim 1 as an aerating booster in a concentration of min. 1% by weight.

16. An aerated confectionery product, bakery product or dairy fillings of claim 15, comprising the fat composition of claim 1 in a concentration of 2-10% by weight.

17. A water barrier between materials with high and low humidity in bakery and confectionery products as well as a paper coating agent comprising the fat composition of claim 1.

18. A cosmetic, pharmaceutical or pharma-like (OTC) product comprising the fat composition of claim 1 as an emollient, excipient and/or consistency giving ingredient.

19. A fat composition for confectionery applications comprising vegetable oil or fat and a Non-LTT fat according to claim 1 in a ratio of 98-5% by weight vegetable oil or fat to 2-95% by weight Non-LTT fat.

20. A fat composition according to claim 19 comprising vegetable oil or fat and a Non-LLT fat in a ratio of 95-10% by weight to 5-90% by weight.

21. A fat composition according to claim 19 comprising vegetable oil or fat and a Non-LTT fat in a ratio of 80-20% by weight to 20-80% by weight.

22. A fat composition of claim 1, wherein the total content of saturated fatty acids measured according to IUPAC 2.301 and 2.304 is between 45-70% by weight.

23. A fat composition of claim 1, wherein the total content of arachidic and behenic acids is 5-35% by weight.

24. A fat composition of claim 1, wherein the total content of palmitic and stearic acids is 25-50% by weight.

25. A fat composition of claim 1, wherein the total content of triglycerides having triglyceride composition (TGC) of C56-C60 measured by number of total carbon atoms of constituent fatty acids according to IUPAC 2.323 is min. 15% by weight.

26. A fat composition of claim 1, wherein the total content of $S_2U$-type triglycerides is min. 35% by weight.

27. A fat composition of claim 1, wherein the total content of lauric acid is max. $S_2U$-type triglycerides is min. 25% by weight.

28. A fat composition of claim 1, wherein the content of diglycerides is max. 5% by weight.

* * * * *

UNITED STATES PATENT AND TRADEMARK OFFICE
CERTIFICATE OF CORRECTION

PATENT NO. : 7,309,508 B2  Page 1 of 1
APPLICATION NO. : 10/832344
DATED : December 18, 2007
INVENTOR(S) : Mogens Bach and Bjarne Juul It is certified that error appears in the above-identified patent and that said Letters Patent is hereby corrected as shown below:

Title Page item 73 should read
--Assignee: AarhusKarlshamn Denmark A/S--

Signed and Sealed this

Tenth Day of June, 2008

JON W. DUDAS
*Director of the United States Patent and Trademark Office*